United States Patent
Cosenza

Patent Number: 5,782,637
Date of Patent: Jul. 21, 1998

[54] PROSTHESIS MOUNTING ARRANGEMENT

[75] Inventor: Frank J. Cosenza, Santa Barbara, Calif.

[73] Assignee: Spiralock Corporation, Madison Heights, Mich.

[21] Appl. No.: 768,504

[22] Filed: Dec. 18, 1996

[51] Int. Cl.⁶ .................................................. A61C 8/00
[52] U.S. Cl. ............................................ 433/173; 433/172
[58] Field of Search ................................. 433/172, 173, 433/174

[56] References Cited

U.S. PATENT DOCUMENTS

| Re. 31,284 | 6/1983 | Holmes | 411/311 |
|---|---|---|---|
| 4,023,914 | 5/1977 | Holmes | 408/220 |
| 4,074,950 | 2/1978 | Holmes | 408/220 |
| 4,076,064 | 2/1978 | Holmes | 151/14 R |
| 4,150,702 | 4/1979 | Holmes | 151/14 R |
| 4,171,012 | 10/1979 | Holmes | 151/14 R |
| 4,181,457 | 1/1980 | Holmes | 408/217 |
| 4,220,187 | 9/1980 | Holmes | 151/20 |
| 4,293,262 | 10/1981 | Holmes | 411/311 |
| 4,351,626 | 9/1982 | Holmes | 411/311 |
| 4,396,321 | 8/1983 | Holmes | 408/217 |
| 4,423,893 | 1/1984 | Holmes | 285/334 |
| 4,547,104 | 10/1985 | Holmes | 408/220 |
| 4,734,002 | 3/1988 | Holmes | 411/311 |
| 4,826,377 | 5/1989 | Holmes | 411/311 |
| 5,269,686 | 12/1993 | James | 433/174 |
| 5,376,004 | 12/1994 | Mena | 433/173 |
| 5,399,090 | 3/1995 | Padros-Fradera | 433/173 |
| 5,431,567 | 7/1995 | Daftary | 433/172 |
| 5,433,606 | 7/1995 | Niznick et al. | 433/173 |
| 5,435,723 | 7/1995 | O'Brien | 433/174 |
| 5,439,380 | 8/1995 | Marlin | 433/173 |
| 5,476,382 | 12/1995 | Daftary | 433/172 |
| 5,607,304 | 3/1997 | Bailey et al. | 433/173 |

*Primary Examiner*—John J. Wilson
*Attorney, Agent, or Firm*—Harness, Dickey & Pierce, PLC

[57] ABSTRACT

A mounting arrangement for interconnecting a prosthesis to a bone of a patient includes a first component adapted for direct attachment to the bone. The first component has a longitudinally extending aperture including an upper portion defined by a smooth surface and a lower portion defined by a plurality of internal threads. The mounting arrangement additionally includes a second component adapted to abut the first component. The second component includes a generally cylindrical channel passing longitudinally therethrough. Further, the mounting arrangement includes a threaded fastener including an upper segment having a smooth surface and a lower segment including a plurality of external threads for meshing engagement with the plurality of internal threads. The upper segment passes through the generally cylindrical channel and it extends partially into the aperture. In one application, the mounting arrangement is intended for interconnecting a dental prosthesis with a human jawbone and permits the dental prosthesis to more effectively accommodate bending forces which develop during normal use by removing the bending forces from the threaded interconnection of the components.

15 Claims, 2 Drawing Sheets

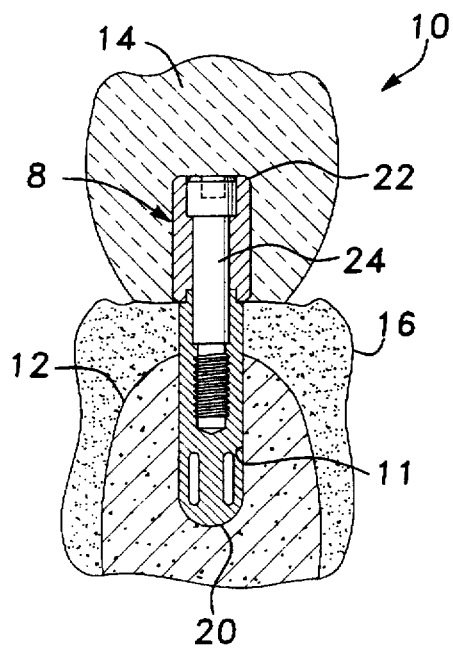
*Fig-1*
*Fig-2*
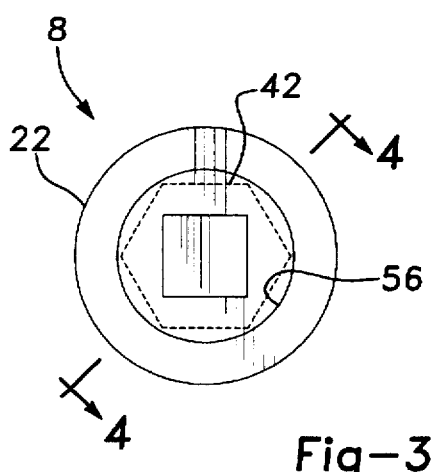
*Fig-3*
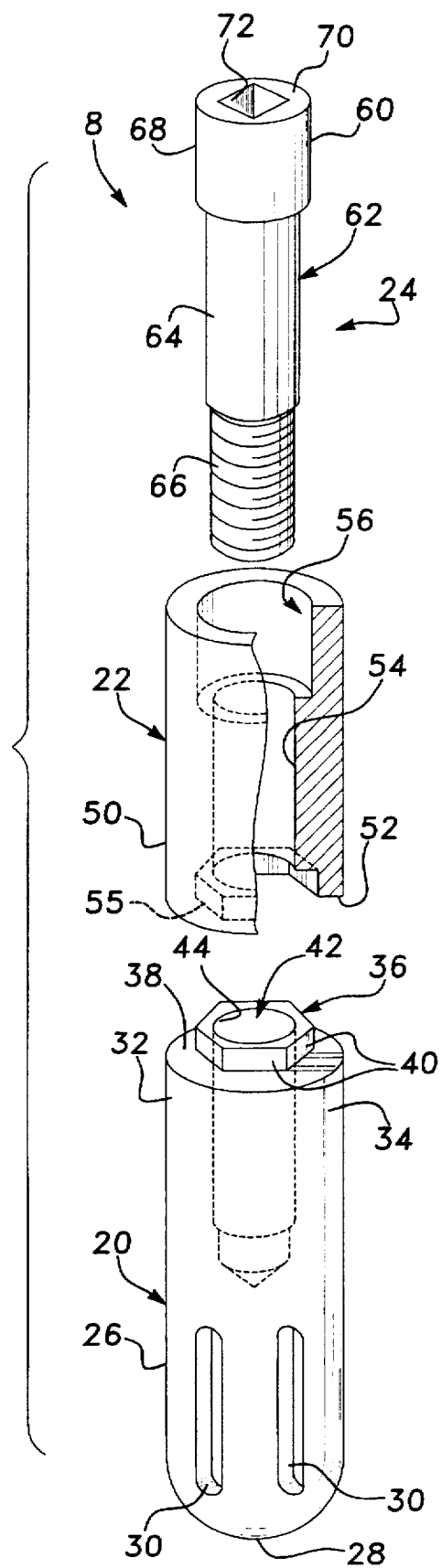

PROSTHESIS MOUNTING ARRANGEMENT

BACKGROUND OF THE INVENTION

1. Field of the Invention

The present invention relates generally to artificial orthopaedic implant prostheses. More particularly, the present invention relates primarily, but not exclusively, to a mounting arrangement for a prosthesis such as a dental prosthesis intended for prolonged or permanent implantation which has a two part construction connected by a threaded fastener.

2. Description of the Prior Art

Human teeth are often extracted or otherwise missing as a result of tooth disease, gum disease, injury, or the like. It is a common practice to functionally and aesthetically replace a lost tooth with a tooth prosthesis. In one manner, the tooth prosthesis is anchored to the remaining adjacent teeth. Provided that the remaining adjacent teeth are well seated in and secured by bone, the use of the remaining adjacent teeth to secure the prosthesis is generally acceptable.

However, there are some occasions in which anchoring is not appropriate. For example, if multiple teeth are missing, the gap may be too large to functionally accept a prosthesis. Further, the remaining adjacent teeth may not be sufficiently secure relative to the jawbone to withstand the additional stresses which will necessarily result from the anchoring of the prosthesis. In such cases where anchoring of the prosthesis to remaining adjacent teeth is not prudent, it is a common practice to surgically install an implant having a post or other securing portion for attachment of the prosthesis. In a known manner, the implant is installed by preparing a socket in the jawbone and inserting the implant into the socket. A post is then connected to the implant and the prosthesis is attached to the post. Typically, interconnection of the components is accomplished with a threaded fastener.

Functional loads imparted to a natural tooth or a prosthesis are principally compression and bending. Current practice in implanting dental implant systems favors non-loading of the implant for an initial period of approximately two (2) to six (6) months during which time the bone supporting the implant recovers from the trauma of the implantation procedure and a firm bond between the implant and the bone is established. This has been conveniently accomplished by utilizing implant systems having two or more parts. Such an implant system is typically embedded in the human mandible, or jawbone, covered with mucosal tissue, and permitted to remain in place while new bone grows around the implant, and into and/or through one or more vent holes in the implant itself. Once the implant has become firmly anchored in the jawbone, the mucosal tissue is reopened, and an abutment or post is connected to the implant using a threaded fastener. A tooth prosthesis is securely connected to the abutment or post.

Successful use of this type and other types of dental implant systems depends on rigid and secure attachment of the implant to the jawbone. Also required is rigid and secure interconnection of the implant and the prosthesis. If either of these two noted requirements is not satisfied, the prosthesis will not function properly and the implant may likely be rejected by the body.

While various prior dental implant systems have attained a significant degree of commercial success, they are not without their associated disadvantages. For example, when the components of known dental implant system are interconnected by a threaded fastener, the threaded fastener will occasionally become loose after the prosthesis has been put into place and the fastener tightened. The loosening is due to normal cyclic forces on the prosthesis which cause the fastener to back out.

To overcome this problem, it is has been previously attempted to provide a dental implant system which includes a locking arrangement for preventing the fastener from backing out. For example, such a locking arrangement for a dental implant system is disclosed in U.S. Pat. No. 5,269,686 to James. James discloses a deformable rod received within a hole that extends diametrically through the threaded fastener. The rod normally protrudes slightly beyond the threads on the fastener so that, when the fastener is received within a threaded opening, the rod will be deformed by the threads.

Recently, various attempts have been made to incorporate locking thread arrangements into dental implant systems. In such arrangements, a threaded fastener of the implant system engages an internally threaded portion of an implant member. The external threads of the fastener and/or the internal threads of the implant member are intended to deform under a predetermined load. Such deformation functions to prevent the fastener from backing out.

Another disadvantage associated with prior known dental implant systems, including but not limited to those discussed above, relates to an inability to adequately withstand bending forces which occur during normal usage. In this regard, bending forces transferred from a tooth prosthesis ultimately to an implanted portion of the implant system are absorbed by the threaded interconnection between the fastener and the implanted portion. These threads are not sufficiently strong to accommodate such bending forces, particularly where deformation of the threads is intended, and frequently subject the implant to fatigue failure from normal usage. In many cases, cyclically applied bending forces to the threaded interconnection between components has resulted in slight movement of the abutment with respect to the implant member. Such relative movement causes improper functioning of the prosthesis and may lead to rejection of the implant by the human body.

SUMMARY OF THE INVENTION

In view of the foregoing above, it is a principal object of the present invention to provide an improved mounting arrangement for a dental implant system which operates to rigidly and securely interconnect a tooth prosthesis with a human jawbone.

It is a related object of the present invention to provide a mounting arrangement for a dental implant system in which the bending forces which develop during normal use are removed from the threads of a fastener, thereby improving bending fatigue of the dental implant system.

It is a more specific object of the present invention to provide a mounting arrangement for a dental implant system in which the bending plane between an implanted component and an abutment is replaced by a closely toleranced threaded fastener shank and aperture.

In a first form, the apparatus of the present invention provides a mounting arrangement for interconnecting a prosthesis to a bone of a patient. The mounting arrangement includes a first component adapted for direct attachment to the bone. The first component has a longitudinally extending aperture including an upper portion defined by a smooth surface and a lower portion defined by a plurality of internal threads. The mounting arrangement additionally includes a second component adapted to abut the first component. The second component includes a generally cylindrical channel passing longitudinally therethrough. Further, the mounting arrangement includes a threaded fastener including a shaft having an upper segment having a smooth surface and a lower segment including a plurality of external threads for meshing engagement with the plurality of internal threads. The upper segment passes through the generally cylindrical channel of the second component and extends partially into the aperture of the first component.

In another form, the apparatus of the present invention provides an orthopaedic implant system adapted for attachment to a bone of a patient. The orthopaedic implant system includes a first component adapted for direct attachment to the bone. The first component has a longitudinally extending aperture including an upper portion defined by a smooth surface and a lower portion defined by a plurality of internal threads. The orthopaedic implant system additionally includes a second component adapted to abut the first component. The second component includes a generally cylindrical channel passing longitudinally therethrough. Further, the orthopaedic implant system includes a threaded fastener having a shaft including an upper segment having a smooth surface and a lower segment including a plurality of external threads for meshing engagement with the plurality of internal threads. The upper segment passes through the generally cylindrical channel and extends partially into the aperture. A prosthesis is attached to the second component.

In a more preferred form, the present invention provides a dental implant system adapted for attachment to a mandible of a patient. The dental implant system includes a first component adapted for direct attachment to the mandible. The first component has a longitudinally extending aperture including an upper portion defined by a smooth surface and a lower portion defined by a plurality of internal threads. The dental implant system additionally includes a second component adapted to abut the first component. The second component includes a generally cylindrical channel passing longitudinally therethrough. Further, the dental implant system includes a threaded fastener having a shaft including an upper segment having a smooth surface and a lower segment including a plurality of external threads for meshing engagement with the plurality of internal threads. The upper segment passes through the generally cylindrical channel and extends partially into the aperture. A prosthesis is attached to the second component.

The preferred embodiment of the present invention thus forms a uniquely simple yet effective arrangement for rigidly and securely interconnecting a tooth prosthesis with the jawbone.

BRIEF DESCRIPTION OF THE DRAWINGS

Further objects, features and advantages of the present invention will become apparent from analysis of the following written specification and accompanying drawings and the appended claims in which:

FIG. 1 is an environmental view of a dental implant system constructed in accordance with the preferred embodiment of the present invention implanted into a socket formed in a human jawbone and shown in cross section;

FIG. 2 is an enlarged and exploded perspective view of the dental implant system of FIG. 1 shown in partial cross section;

FIG. 3 is a top plan view of the dental implant system of FIG. 1 illustrated in an assembled condition;

DETAILED DESCRIPTION OF THE PREFERRED EMBODIMENT

Figure 4:
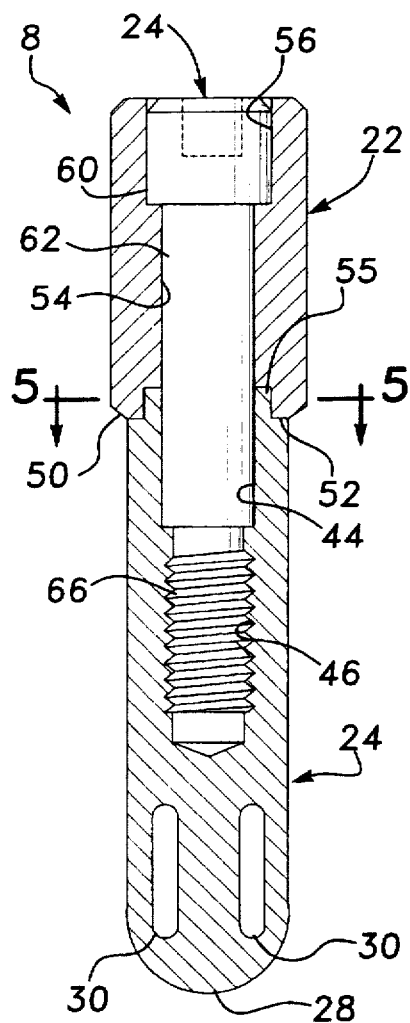
FIG. 4 is a cross-sectional view of the dental implant system of FIG. 1 taken along the line 4—4 of FIG. 3.
Figure 5:
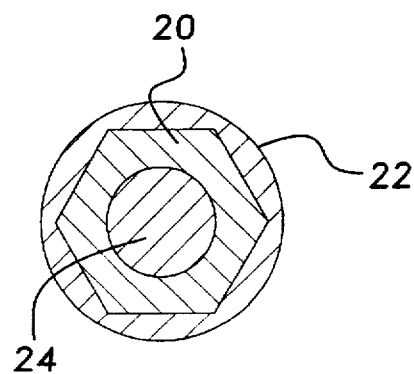
FIG. 5 is a cross-sectional view taken along the line 5—5 of FIG. 4.

As required, a detailed embodiment of the present invention is disclosed herein. However, it is to be understood that the disclosed embodiment is merely exemplary of the invention which may be embodied in various forms. Therefore, specific functional and structural details disclosed herein are not to be interpreted as limiting, but merely as a basis for the claims and as a representative basis for teaching one skilled in the art to variously employ the present invention in virtually any appropriately detailed structure.

Turning now generally to the drawings, a mounting arrangement constructed in accordance with the teachings of the preferred embodiment of the present invention is illustrated and generally identified with reference number 8. In general, the mounting arrangement is designed for rigidly and securely interconnecting a prosthesis and a human bone. In the exemplary application shown in FIG. 1, the mounting arrangement is incorporated into a dental implant system 10 which is specifically intended to be embedded in a prepared tooth socket 11 in a human mandible, or jawbone 12, for secure attachment thereto.

In the exemplary embodiment illustrated, the mounting arrangement 8 operates to functionally and aesthetically replace an extracted or otherwise missing tooth (not shown). To this end, the dental implant system 10 includes a tooth prosthesis 14 of generally conventional construction. It will be appreciated that the tooth prosthesis 14 illustrated in FIG. 1 is exemplary in nature and may be of various other constructions depending upon the tooth or teeth being replaced by the dental implant system 10. The tooth socket 11 is prepared in a known manner to generally conform to the shape of the implant system 10 to thereby minimize loss of bone 12 and facilitate bone ingrowth. Briefly, the dental implant system 10 is implanted through opened gingival tissue 16 and into the prepared tooth socket 11 in the jawbone 12.

With continued reference to FIG. 1 and additional reference to FIGS. 2 through 6, the mounting arrangement 8 of the present invention is shown to generally include an implant fixture 20, an abutment member 22 and a fastener 24 interconnecting the implant fixture 20 and the abutment member 22. The implant fixture 20 in preferably constructed of titanium or other suitable material and has a generally cylindrical shape and an unthreaded external sidewall 26. Adjacent a lower end 28, the implant fixture 20 is shown to include a plurality of oval cross-vents 30 that functions to form internal openings in the implant fixture 20. The exemplary embodiment includes two (2) such cross-vents 30 which operate to facilitate bone ingrowth and thereby strengthen the interconnection of the mounting arrangement 8 with the jawbone 12. In the preferred embodiment, the external sidewall 26 of the implant fixture 20 is treated in a manner well known in the art to include a toughened surface. For example, the external sidewall 26 may be treated by a plasma spray or other biologically inert coating.

Adjacent an upper end 32 of the sidewall 26 of the implant fixture 20, the implant fixture 20 is constructed to include a smooth sidewall region 34. Above the smooth sidewall region 34, at the top of the implant fixture 20, is a polygonal-shaped male projection 36 which is generally centered on a flat upper surface 38. The polygonal-shaped male projection 36 is preferably hexagonal in shape, including six (6) sides 40, and defines a longitudinally extending aperture 42 which extends downwardly into the implant fixture 20. The longitudinally extending aperture 42 is threaded along at least a portion of its interior surface for threaded engagement with the fastener 24. In the preferred embodiment, the longitudinally extending aperture 42 includes an upper portion 44 defined by a smooth surface and a lower portion defined by a plurality of external threads 46.

As noted above, the implant fixture 20 is shaped so that bone tissue will be conserved upon preparation of the conforming socket 11 in the jawbone 12 for implantation. While the illustrated embodiment has a smooth exterior surface 26, it will be appreciated by those skilled in the art that the exterior surface 26 may alternatively have other shapes such as threaded screw-like shapes, conical shapes and blade shapes. In addition, the lower portion of the implant fixture 20 may be machined to have the same profile as an extracted tooth and may be implanted in the cavity left after extraction.

The upper abutment member 22 is formed similar to the implant fixture 20 to include a generally cylindrical, unthreaded outer wall surface. As shown most clearly in the cross-sectional view of FIG. 4, the abutment member 22 tapers slightly adjacent a lower end 50. The lower end 50 has an outer diameter substantially identical to the outer diameter of the implant fixture 20. The abutment member 22 is also formed at its lower end 50 to include a flat lower surface 52. An aperture 54 longitudinally passes through an entire length of the abutment member 22. A hexagonal recess 55 is formed in the flat lower surface 52 of the abutment member 22 and is centered around the aperture 54. The six sides of the hexagonal recess 55 are all substantially perpendicular to the flat lower surface 52. Adjacent an upper end, the abutment member 22 includes an enlarged cylindrical bore 56 coincentrically formed with the aperture 54. The aperture 54 is of sufficient diameter to permit the threaded fastener 24 to pass through and to enter the aperture 42 of the implant fixture 20.

In the embodiment illustrated, the threaded fastener 24 is illustrated to generally include a head 60 and a shank 62. The shank 62 has an upper segment 64 having a smooth surface and a lower segment including a plurality of external threads 66. The head 60 includes a generally cylindrically outer surface 68 and a flat top surface 70. An aperture 72 is formed in the top surface 70 and extends downwardly. In the exemplary embodiment illustrated, the aperture 72 is rectangular in shape, and preferably square. However, it will be appreciated by those skilled in the art that the aperture 72 can alternatively be of hexagonal shape or other suitable shape. The rectangular aperture 72 is intended to receive a rectangular tool for driving the threaded fastener 24.

Significantly, the unthreaded upper segment 64 of the shank 62 of the threaded fastener 24 is of sufficient length to extend a substantial distance into the aperture 42 of the implant fixture 20. Further significantly, the unthreaded upper segment 64 of the shank 62 is closely toleranced to both the aperture 54 of the abutment member 22 and the aperture 42 in the implant fixture 20. In the preferred embodiment, this tolerance is less than 0.001 inch. In one application, the diameter of the upper segment 64 of the shaft 62 is approximately 0.076 inch in diameter. Further in this application, the upper segment 64 of the shank 62 extends into the aperture 42 a distance equal to or greater than the diameter of the upper segment 64. In the embodiment illustrated, the upper segment 64 extends into the upper portion 42 of the aperture 44 a distance equal to approximately 1.5 times the diameter of the upper segment 64. As a result, bending forces of which typically are transferred from the abutment member 22 to the threaded portion of the fastener 24 are absorbed by the shank 62 and the sidewalls of the apertures 42 and 54, thereby enhancing the bending fatigue of the dental implant system 10.

Figure 6:
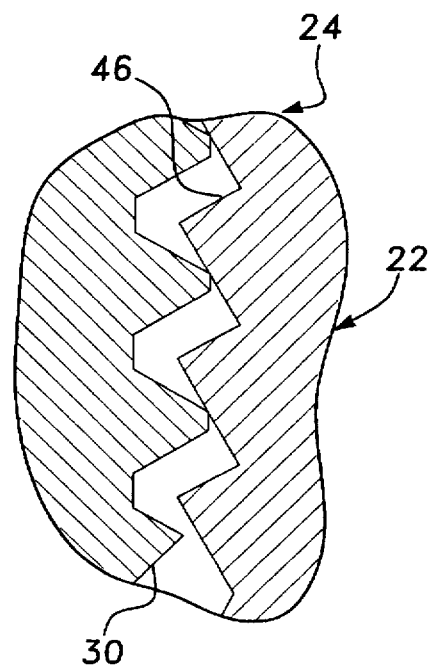
FIG. 6 is an enlarged view of the internal thread of the implant fixture and external thread of the threaded fastener when in free-running relationship to each other.

With specific reference to the cross-sectional view of FIG. 6, the threaded interconnection between the fastener 24 and the aperture 42 is preferably shown to be of a locking design. More particularly, the threaded portion 46 of the aperture 42 of the implant fixture 20 includes a plurality of internal threads 46 which are in normal free-running association with the plurality of external threads 66 of the fastener 24. In use, at least one of the plurality of internal threads 46 and the plurality of external threads 66 is intended to deform under a predetermine torque load applied to the fastener 24. The fastener 24 is preferably, although not necessarily, constructed of titanium, stainless steel, or other suitable inert material suitable for implantation.

The threaded interconnection between the threaded fastener 24 and the implant fixture 20 discussed above is but one suitable form. Other locking thread constructions which may alternatively be incorporated are shown and described in the following commonly owned U.S. Pat. Nos: 4,076,064; 4,150,782; 4,171,012; 4,220,187 4,423,893; 4,351,626 4,547,104; 4,734,002; 4,826,377 and Re. 31,284. These patents are incorporated by reference as if fully set forth herein. Further, it will be appreciated by those skilled in the art that certain applications of the present invention may not require a locking thread arrangement.

In the exemplary embodiment, the tooth prosthesis 14 is fixedly bonded to the abutment 22 with a cement or adhesive. Alternatively, the prosthesis 14 may be attached to the abutment 22 in any other suitable manner well known in the art. While not specifically illustrated, the prosthesis includes a central aperture which longitudinally extends therethrough for providing access to the fastener 24. Once the prosthesis 14 is in place, this aperture can be filled in a conventional manner.

While the above detailed description describes the preferred embodiment of the present intention, it should be understood that the present invention is susceptible to modification, variation and alteration without deviating from the scope and fair meaning of the subjoined claims. In this regard, it will be understood that the teachings of the present invention may be modified for use with various other types of prosthetic devices.

What is claimed is:

1. A mounting arrangement for interconnecting a prosthesis to a bone of a patient, the mounting arrangement comprising:

a first component adapted for direct attachment to the bone, said first component including a longitudinally extending aperture having an upper portion with a cylindrical cross section with a constant diameter defined by a smooth surface and a lower portion defined by a plurality of internal threads;

a second component adapted to abut said first component, said second component including a generally cylindrical channel passing longitudinally therethrough; and a threaded fastener having a shaft including an upper segment having a smooth surface having a cylindrical cross section with a constant diameter and a lower segment including a plurality of external threads for meshing engagement with said plurality of internal threads, said upper segment passing through said generally cylindrical channel and extending partially into said aperture;

wherein said upper segment of said shaft of said threaded fastener and said upper portion of said longitudinally extending aperture are closely toleranced so as to prevent bending forces from being transmitted to said plurality of internal threads and said plurality of external threads.

2. The mounting arrangement for interconnecting a prosthesis to a bone of a patient of claim 1, wherein at least one of said plurality of internal threads and said plurality of external threads is intended to deform upon application of a predetermined torque to said threaded fastener.

3. The mounting arrangement for interconnecting a prosthesis to a bone of a patient of claim 1, wherein said threaded fastener includes a head defining a generally rectangular recess.

4. The mounting arrangement for interconnecting a prosthesis to a bone of a patient of claim 1, wherein said upper segment of said shaft of said threaded fastener and said upper portion of said longitudinally extending aperture are substantially in constant engagement so as to prevent bending forces from being transmitted to said plurality of external threads and said plurality of internal threads.

5. The mounting arrangement for interconnecting a prosthesis to a bone of a patient of claim 1, wherein said first component includes an upwardly extending polygonal male portion and further wherein said second component includes a polygonal recess adapted to receive said upwardly extending polygonal male portion.

6. An orthopaedic implant system adapted for attachment to a bone of a patient, the orthopaedic implant system comprising:

a first component adapted for direct attachment to the bone, said first component including a longitudinally extending aperture having an upper portion defined by a smooth surface and a lower portion defined by a plurality of internal threads, said upper portion having a cylindrical cross section with a constant diameter;

a second component adapted to abut said first component, said second component including a generally cylindrical channel passing longitudinally therethrough;

a threaded fastener having a shaft including an upper segment having a smooth surface and a cylindrical cross section with a constant diameter and a lower segment including a plurality of external threads for meshing engagement with said plurality of internal threads, said upper segment passing through said generally cylindrical channel and extending partially into said aperture; and a prosthesis attached to said second component;

wherein said upper segment of said shaft of said threaded fastener and said upper portion of said longitudinally extending aperture are closely toleranced so as to prevent bending forces from being transmitted to said plurality of external threads and said plurality of internal threads.

7. The orthopaedic implant system adapted for attachment to a bone of a patient of claim 6, wherein at least one of said plurality of internal threads and said plurality of external threads is intended to deform upon application of a predetermined torque to said threaded fastener.

8. The orthopaedic implant system adapted for attachment to a bone of a patient of claim 6, wherein said threaded fastener includes a head defining a generally rectangular recess.

9. The orthopaedic implant system adapted for attachment to a bone of a patient of claim 6, wherein said upper segment of said shaft of said threaded fastener and said upper portion of said longitudinally extending aperture are substantially in constant engagement so as to prevent bending forces from being transmitted to said plurality of external threads and said plurality of internal threads.

10. The orthopaedic implant system adapted for attachment to a bone of a patient of claim 9, wherein said first component includes an upwardly extending polygonal male portion and further wherein said second component includes a polygonal recess adapted to receive said upwardly extending polygonal male portion.

11. A dental implant system adapted for attachment to a mandible of a patient, the dental implant system comprising:

a first component adapted for direct attachment to the mandible, said first component including a longitudinally extending aperture having an upper portion defined by a smooth surface and a lower portion defined by a plurality of internal threads, said upper portion having a cylindrical cross section with a constant diameter;

a second component adapted to abut said first component, said second component including a generally cylindrical channel passing longitudinally therethrough;

a threaded fastener having a shaft including an upper segment having a smooth surface and a lower segment including a plurality of external threads for meshing engagement with said plurality of external threads, said upper segment passing through said generally cylindrical channel and extending partially into said aperture, said upper segment having a cylindrical cross section with a constant diameter; and a tooth prosthesis attached to said second component;

wherein said upper segment of said shaft of said threaded fastener and said upper portion of said longitudinally extending aperture are closely toleranced so as to prevent bending forces from being transmitted to said plurality of external threads and said plurality of internal threads.

12. The dental implant system adapted for attachment to a mandible of a patient of claim 11, wherein at least one of said plurality of internal threads and said plurality of external threads is intended to deform upon application of a predetermined torque to said threaded fastener.

13. The dental implant system adapted for attachment to a mandible of a patient of claim 11, wherein said threaded fastener includes a head defining a generally rectangular recess.

14. The dental implant system adapted for attachment to a mandible of a patient of claim 11, wherein said upper segment of said shaft of said threaded fastener and said upper portion of said longitudinally extending aperture are substantially in constant engagement so as to prevent bending forces from being transmitted to said plurality of external threads and said plurality of internal threads.

15. The dental implant system adapted for attachment to a mandible of a patient of claim 14, wherein said first component includes an upwardly extending polygonal male portion and further wherein said second component includes a polygonal recess adapted to receive said upwardly extending polygonal male portion.

* * * * *